US008865450B2

(12) United States Patent
Reiter et al.

(10) Patent No.: US 8,865,450 B2
(45) Date of Patent: Oct. 21, 2014

(54) METHOD FOR PRODUCING CONTINUOUS CELL LINES (75) Inventors: Manfred Reiter, Vienna (AT); Wolfgang Mundt, Vienna (AT); Simone Feigl, Vienna (AT); Simone Von Fircks, Vienna (AT)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 0 days.

(21) Appl. No.: 12/390,187

(22) Filed: Feb. 20, 2009

(65) Prior Publication Data
US 2009/0215123 A1 Aug. 27, 2009

Related U.S. Application Data (60) Provisional application No. 61/067,174, filed on Feb. 25, 2008.

(51) Int. Cl.
C12N 7/00 (2006.01)
C12N 15/01 (2006.01)

(52) U.S. Cl.
CPC ...... *C12N 15/01* (2013.01); *C12N 2760/16151* (2013.01); *C12N 7/00* (2013.01); *C12N 2710/24151* (2013.01); *C12N 2510/04* (2013.01)
USPC ........ 435/235.1; 435/325; 435/440; 435/448; 435/460

(58) Field of Classification Search
USPC .............. 435/235.1, 325, 440, 448, 446, 460
See application file for complete search history.

(56) References Cited

U.S. PATENT DOCUMENTS

| 2006/0270017 A1 | 11/2006 | Reiter et al. | |
|---|---|---|---|
| 2007/0212770 A1 | 9/2007 | Grillberger et al. | |
| 2007/0283453 A1* | 12/2007 | Rodriguez Cimadevilla et al. | 800/10 |
| 2008/0227146 A1* | 9/2008 | Sandig et al. | 435/69.1 |
| 2009/0239297 A1* | 9/2009 | Pain et al. | 435/349 |

FOREIGN PATENT DOCUMENTS

| EP | 0920491 B1 | 5/2007 |
|---|---|---|
| EP | 1985305 A1 | 10/2008 |
| WO | WO-2003/066093 A1 | 8/2003 |
| WO | WO 2005/042728 | * 5/2005 |
| WO | WO-2005/042728 | 5/2005 |
| WO | WO 2006/108846 | * 10/2006 |
| WO | WO-2008/129058 A1 | 10/2008 |

OTHER PUBLICATIONS

Cowen et al 1988; The propagation of avian viruses in a continuous cell line (QT35) of Japanese quail origin; Avian Diseases, pp. 282-297.*
Voeten et al., Characterization of high-growth reassortant influenza A viruses generated in MDCK cells cultured in serum-free medium Vaccine; vol. 17, Issues 15-16, Apr. 9, 1999, pp. 1942-1950.*
Hornemann et al., 2003, Replication of modified vaccinia virus Ankara in primary chicken embryo fibroblasts requires expression of the interferon resistance gene E3L. J. Virol. pp. 8394-8407.*
Porter et al., 2006; DNA Repair; Telomerase-immortalized human fibroblasts retain UV-induced mutagenesis and p53-mediated DNA damage responses. pp. 61-70.*
Vijg et al., UV-induced DNA excision repair in rat fibroblasts during immortalization and terminal differentiation in vitro Experimental Cell Research vol. 167, Issue 2, Dec. 1986, pp. 517-530.*
Klenk et al., Activation of influenza A viruses by trypsin treatment. *Virology.* 68(2): 426-39 (1975).
International search report from PCT/US2009/034732 dated Feb. 8, 2010.
Kistner et al., "Development of a mammalian cell (Vero) derived candidate influenza virus vaccine," Vaccine, Butterworth Scientific Guildford, G.B. 16(9-10):960-968 (1998).
Milo, et al., "Neoplastic Transformation of Human Epithelial Cells In-Vitro After Exposure to Chemical Carcinogens," Cancer Research 41(12):5096-5102 (1981).
Rhim, "Development of human cell lines from multiple organs," Annals of the New York Academy of Sciences, 919:16-25 (2000).
Lee et al., Enhancement of UVB radiation-mediated apoptosis by knockdown of cytocolic NADP+-dependent isocitrate dehydrogenase in HaCaT cells. *BMB Reports* 47(4): 209-14 (2014).
Shorrocks et al., The dose rate of UVA treatment influences the cellular response to HaCaT keratinocytes. *J. Investig. Dermatol.* 128: 685-93 (2007).

* cited by examiner

*Primary Examiner* — Maria Leavitt
(74) *Attorney, Agent, or Firm* — Marshall, Gerstein & Borun LLP (57) ABSTRACT The present invention relates to a method for production of continuous cell lines comprising providing living cells of an animal or a human, irradiating said cells with UV light, proliferating said cells and selecting multiplying cells as cells of a continuous cell line.

17 Claims, 3 Drawing Sheets

Fig. 1

Fig. 2 after passage before confluence

METHOD FOR PRODUCING CONTINUOUS CELL LINES

FIELD OF THE INVENTION

The present invention relates to methods for producing cell lines.

BACKGROUND OF THE INVENTION

Cell lines have become a valuable tool for vaccine manufacturing. The production of some important vaccines and viral vectors is still done in embryonated chicken eggs or primary chicken embryo fibroblasts. Primary avian tissue for virus replication is provided by SPF (specific pathogen free) production plants. SPF derived tissues are expensive and the quality of the supply material is often hard to control. Therefore, inconsistency and shortage in supply are the most predominant disadvantages of the technologies based on SPF eggs. The same is true for approaches where primary fibroblast monolayer cultures are used. To multiply cell lines indefinitely, the cells need to be immortalized. Most immortalized cell lines currently in use are descendants of cancer cells or of fused hybridoma cells. However, the later technology is limited to fusion with myeloma cells. No general technology exists that can generate immortalized cells of different types.

SUMMARY OF THE INVENTION

It is an object of the present invention to produce a continuous cell from non-continuous cell material. In particular, the goal was to provide continuous cell lines that have the potential to proliferate without the introduction of foreign viral genes.

Therefore, the present invention provides a method for production of continuous cell lines comprising providing living cells of an animal or a human, irradiating said cells with UV light, proliferating said cells and selecting cells capable to proliferate after at least 20 passages as cells of a continuous cell line.

Such a continuous cell line is culture of cell that can be propagated and used for the recombinant expression of biomolecules such as proteins, or for the manufacture of viral products such as viral antigens or a whole virus population, in particular for vaccination purposes.

Therefore, the present invention also provides a method of producing a virus comprising providing cells of a continuous cell line obtainable by the inventive method, infecting said cells with said virus, propagating said virus in said cells and collecting said virus.

In another aspect the invention provides a method of producing a recombinant gene product comprising providing cells of a continuous cell line obtainable by the inventive method, transfecting the cells with a nucleic acid encoding said gene product, expressing said gene product and, optionally, collecting said gene product.

In a further aspect the invention provides a continuous cell line obtainable by the method of providing living cells of an animal or a human, irradiating said cells with an effective dose of UV light, proliferating said cells and selecting cells capable of proliferating after at least 20 passages as cells of said continuous cell line.

DETAILED DESCRIPTION OF THE INVENTION

The present invention provides the production of a continuous cell line through UV treatment of cells.

A cell line is a population of cells formed by one or more subcultures of a primary cell culture. Each round of subculturing is referred to as a passage. When cells are subcultured, they are referred to as having been passaged. A specific population of cells, or a cell line, can be characterized by the number of times it has been passaged. The primary culture is the first culture following the isolation of cells from tissue. Following the first subculture, the cells are described as a secondary culture (one passage). After the second subculture, the cells become a tertiary culture (passage 2), and so on. It will be understood by those of skill in the art that there may be many population doublings during the period of passaging; therefore, the number of population doublings of a culture is greater than the passage number. The expansion of cells (i.e., the number of population doublings) during the period between passaging depends on many factors, including but not limited to the seeding density, substrate, medium, growth conditions, and time between passaging. Culturing can be performed by inoculation of a cell medium, letting the cells grow until a confluent cell culture or a continuous film is formed by the cells and inoculating a new cell medium with a portion of the confluent cells. Nevertheless, passaging is a tool to evaluate the capability to propagate. Normally, cells, including non-irradiated cells, isolated from a tissue can be passaged about 10-20 times until they reach a state where no further propagation or cell doubling occurs. The cells then enter a senescent state from which no further subcultures can be obtained. Contrary thereto continuous cell lines are capable to propagate after more than 20 passages, such as after more then 22, 24, 26, 28, 30, 32, 34, 36, 38, 40, 42, 44, 46, 48, 50, 55, 60, 65, 70, 75 or 80 passages. It has now been found by the inventors that such a continuous cell line which can be passaged multiple times past the $20^{th}$ passage, in particular immortalized cells, can be obtained through alteration of cells by UV treatment, i.e. by irradiating these cells with an effective dose of UV light. The terms "effective dose of UV light" according to the present invention shall be the amount of irradiation needed for transforming the non-continuous cell lines into continuous cell lines. The effective dose of UV light ranges from the minimum dosage required for such transformations to the maximum dosage which is tolerated by these cells without lethal consequences for the cell culture as a whole. It is clear that above or under the effective dose limits continuous cell lines cannot be obtained. The skilled man in the art can easily determine optimum effective dosages for each cell line on the basis of the information and guidance contained herein with routine optimization. The cells may be primary cells or cells capable of propagation after a few passages. Culturing of the cell lines can be performed with standard cell culture techniques, such as in T-flask systems or roller bottle systems, or in stirred tank or other bioreactor formats. In several embodiments of the invention, the culture is adapted to and held under serum-free conditions.

In the present application the term "UV light" means ultraviolet radiation having a wavelength of from 10 to 400 nm, in particular 100 to 400 nm. The UV light may be selected from the group consisting of UV C (100 to 280 nm), UV B (280 to 320 nm), and UV A (320 to 400 nm). In some embodiments of the invention, the wavelength is between 200 and 300 nm. Photosensitizing agents such as those which intercalate into the DNA and which are activated by UV light may be used to enhance the altering effect of the UV radiation, although they are not necessary in all embodiments of the invention. In one embodiment of the present invention the UV light is UV C having a wavelength of from about 100 to about 280 nm. In another embodiment of the present invention the UV light has a wavelength of from about 240 to about 290 nm. In another embodiment of the present invention about 85% or more of the UV light has a wavelength of about 254 nm.

Without being bound by any theory it is believed that the UV light alters the genetic material of a cell, which introduces mutations. While such alterations can generally be repaired by the cell's repair mechanisms, some alterations might remain. These alterations can introduce lethal mutations and also alterations which result in cell immortalization. From UV irradiation experiments an optimal dosage can be selected which results in a significant portion of cells which are immortalized and can be cultured. After passaging, it is believed that only viable cells which are capable of multiplying are selected, which are expected to have only minor alterations with at least one alteration which results in immortalization. A significant portion of the irradiated cells will not be immortalized but gain different alterations, leading to apoptotic or necrotic cells. However, in principle, only one cell with the alteration inducing immortalization is sufficient to obtain a continuous cell culture, as this cell will continue to propagate and survive through the multiple rounds of passaging as described herein.

The UV light emission may be a continuous form of UV light emission, e.g. mercury lamp technology, or pulsed UV light, e.g. monochromatic laser technology. The desired UV intensity may be generated by combining two or more lamps. At least two irradiation procedures may be combined with a pause in between. The subject matter of the invention encompasses any effective dosage of UV light, i.e. any dosage of UV light which alters a cell to proliferate continuously. The effective dosage may depend on a variety of factors which are generally known in the field, e.g. the physical parameters of the UV irradiation chambers, such as size and diameter of the lamp and the chamber, distance between the cell containing medium and the UV light source, light absorption and reflection properties of the material of the chamber. In particular embodiments of the invention, the cells are irradiated in a monolayer, one cellular layer on a surface. By the same token, the wavelength and intensity of the UV light as well as the contact time the cell is exposed to the UV light are also critical for the effective dosage. Furthermore, the effective dosage is also influenced by the cell itself, the medium containing the virus and their light absorption properties. In various embodiments of the invention, the effective dosage is sufficient to alter at least 20%, 30%, 40%, 50%, 60%, 70%, 80%, 90% or 100% of cells contained in the sample, and in other embodiments the effective dosage is sufficient to alter the cells to a level where at least 10% of the cells are either altered to grow continuously. 10% to 90% of the cells may be killed by the irradiation. In certain embodiments of the invention, a sample containing the cells is exposed to an effective dosage of at least about 5, 10, 15, 20, 25, 30, 35, 40, 45, 50, 55, 60, 65 or 70 mJ/cm$^2$. In some embodiments the effective dosage is up to about 500, 450, 400, 350, 300, 250, 200, 180, 150, 130 or 105 mJ/cm$^2$. In particular embodiments of the invention, the UV dosage is between about 70 and 105 mJ/cm$^2$. In some embodiments, these dosages are employed by UV C light. The term "about" refers to the property of common UV lamps which do not provide a discrete UV light at a single wavelength (as in lasers) but have a gauss shaped spectrum also emitting light in nearby wavelengths. In embodiments utilizing some of these lamps, "about" refers to a deviation of the wavelength value of 10%.

Before or after irradiation or passaging, the cell line is can be further selected for fulfilling quality control criteria such as sterility, free of mycoplasma contamination, free of adventitious virus contamination, and/or passing the F-Pert test for the presence of reverse transcriptase activity, as well as other quality control criteria used in the art for selecting cell lines for medical biotechnology uses. In this sense "free of" is to be understood that contaminations are reduced to be below the detection limit of current quality test procedures. Since the present technology can generate continuous cell lines without the use of viral vectors or introduction of retroviruses, the inventive cell lines are often free of any retroviral activity, as can be tested by an assay for reverse transcriptase activity. However, such retroviral activity may be specifically introduced into the cell lines of the invention by molecular engineering techniques for the purposes of, for example, production of viruses or proteins in the cell lines.

The cell line can be of any eukaryotic cell, particularly of a higher organism, such as in fish, avian, reptile, amphibious or mammal cells and even insect or plant cells. Some embodiments utilize mammal cells such as of hamster, mice, rat, dog, horse, cow, primate, or human; other embodiments utilize avian cells such as of chicken, duck, canary, parrot, quail, ostrich, emu, turkey or goose. In general, any bird species could be a source of avian cells for use in the invention. In some embodiments, it is advantageous to utilize a less frequently domesticated specie (such as quail or emu) to avoid potential contamination of stock tissues with viruses prevalent in more commonly domesticated species (such as chickens.)

The irradiated cells can be of any type of tissue. In some embodiments the tissue is derived from an embryo. In many embodiments, a mixed culture of more than one type of tissue is used, as can be obtained by disintegrate tissue or multiple tissues. In further embodiments the cells are of the umbilical cord of an embryo. The irradiated cells can be or the tissue(s) can be of or include e.g. endothelial cells, epithelial cells, pluripotent or totipotent stem cells, embryonic stem cells, neuronal cells, renal cells, liver cells, muscle cells, colon cells, leukocytes, lung cells, ovary cells, skin cells, spleen cells, stomach cells, thyroid cells, vascular cells, pancreatic cells, and/or precursor cells thereof and combinations thereof.

In many embodiments the cells are attached to a surface during irradiation or during culturing. Culturing on a surface is especially suitable for endothelial cells, whereby the cells can be further selected for fulfilling further quality criteria such as their capability to form monolayers, which can be hampered if the UV dosage introduces too much damaging alteration. On such a surface the cells may form monolayers. In particular the cells are cultured or irradiated on a microcarrier. Alternatively the cells may be either irradiated or cultured or both in suspension. Cells which are initially irradiated or cultured on a surface may later be adapted to growth in suspension culture.

In another aspect the present invention provides a method of producing a virus comprising providing cells of a continuous cell line obtainable by the inventive method, infecting said cells with said virus, propagating said virus in said cells and collecting said virus.

In the present invention, the viruses to be produced are selected from enveloped or unenveloped DNA or RNA viruses, with single or double (DNA) stranded genomes, sense or antisense, continuous or segmented. The viruses may be selected from the group consisting of baculoviruses, poxviruses, adenoviruses, papovaviruses, parvoviruses, hepadnaviruses, coronaviruses, flaviviruses, togaviruses, astroviruses, picornaviruses, retroviruses, orthomyxoviruses, filoviruses, paramyxoviruses, rhabdoviruses, arenaviruses, and bunyaviruses. In some embodiments of the invention, the viruses are selected from the group of enveloped viruses, including, flaviviruses, togaviruses, retroviruses, coronaviruses, filoviruses, rhabdoviruses, bunyaviruses, orthomyxoviruses, paramyxoviruses, arenaviruses, hepadnaviruses, herpesviruses, and poxviruses. In other embodiments, the viruses are enveloped viruses such as influenza, including influenza A, B or C, West Nile Virus, Vaccinia Virus, Modified Vaccinia Virus, or Ross River viruses. In other embodiments of the invention, the viruses are selected from the group of enveloped RNA viruses, including, flaviviruses, togaviruses, retroviruses, coronaviruses, filoviruses, rhabdoviruses, bunyaviruses, orthomyxoviruses, paramyxoviruses, and arenaviruses. In particular embodiments the virus is MVA (modified vaccinia virus Ankara), TBE (tick-borne encephalitis) virus, Yellow fever virus, West Nile virus, New Caledonia virus or an influenza virus.

After the collecting step, the virus can be inactivated by any known means for virus inactivation, e.g. as disclosed in the US publication number 2006/0270017 A1, which is incorporated herein by reference. In particular, inactivation can be performed by formaldehyde treatment and/or UV irradiation, alone or in combination.

In general, serum or serum-derived substances, such as, e.g., albumin, transferrin or insulin, may comprise unwanted agents that can contaminate the cell cultures and the biological products obtained thereof. Furthermore, human serum derived additives have to be tested for all known viruses, including hepatitis viruses and HIV which can be transmitted via serum. Therefore, according to some embodiments of the inventive method, the cells of the cell line are adapted for growth in serum free media, e.g. they are selected for their capability to grow in serum free media. The media may be free of serum or serum fractions, or also in general blood constituents. Media for these embodiments of the invention are selected from DMEM/HAM's F12, RPMI, MEM, BME, Waymouth's medium, in particular an oligopeptide- or protein-free medium as described in the US 2007/0212770 which is incorporated herein by reference in its entirety, or a combination thereof. Said oligopeptide free medium may be free of blood proteins or oligopeptides with a size of more than 15, 14, 13, 12, 11, 10, 9, 8, 7, 6, 5, or 4 amino acids but may comprise glutathione. The protein-free medium is substantially free of proteins but may contain proteins produced by the cell lines or proteases. In particular the medium may also comprise a polyamide as growth promoting agent and/or be a chemically defined medium as described in the US 2007/0212770. The term "chemically defined" means that the medium does not comprise any undefined supplements, such as, for example, extracts of animal compo-nents, organs, glands, plants, or yeast. Accordingly, each component of a chemically defined medium is accurately defined. The chemically defined media are substantially free of proteins, or cell hydrolysates but may contain proteins produced by the cell line or proteases. Examples of such media are given in "A guide to Serum-Free Cell Culture", GIBCO cell culture (2003).

These media, including the serum free medium, the oligopeptide free medium or the chemically defined medium, may also comprise glutathione and/or proteases, in particular trypsin such as porcine or recombinant trypsin prior or after virus inoculation (Klenk et al. (1975) Virology, 68: 426-439). Such proteases may also be required during culturing of the cell lines since cells attached to a surface by exhibit strong to very light adherence. Strongly attached cells can be detached by proteases and/or chelating agents such as EDTA (Doyle et al. Chapter 4: Core Techniques, in: Cell & Tissue Culture: Laboratory Procedures, ECACC, John Wiley & Sons, Chichester (1996)). Furthermore the medium, in particular the protein free medium, may comprise plant or yeast hydrolysates prior or after inoculation. Of course the medium is also expected to comprise proteins or metabolic products produced by the inventive cell lines.

The cell lines obtainable by the inventive method are generally non-tumorigenic and/or non-carcinogenic. In some embodiments the cells of the cell lines are tested and selected for to pass quality test such as the F-pert test.

In a further aspect the invention provides a method of producing a recombinant gene product comprising providing cells of a continuous cell line obtainable by the inventive method, transfecting the cells with a nucleic acid encoding said gene product, expressing said gene product and optionally collecting said gene product. The nucleic acid may be DNA, RNA or PNA. In addition to the gene, the nucleic acid may comprise promoters for expression in the cell, and selection markers.

In a further aspect the invention provides a continuous cell line obtainable by the method of providing living cells of an animal or a human, irradiating said cells with an effective dose of UV light, proliferating said cells and selecting cells capable to proliferate after at least 20 passages as cells of said continuous cell line. The inventive cell lines also include the progeny of such produced cell lines. In particular the cell line is defined as being obtainable by the embodiments of the method described herein. The obtainable continuous cell lines may have characteristic features such as telomere activity of specific caryotypes associated with the W irradiation necessary to produce the continuous cell line. In particular embodiments of the invention the cells of the cell line are non-tumorigenic and/or non-carcinogenic and in particular also pass quality tests such as the F-pert test.

In particular embodiments the cell line is a cell line deposited at the ECACC with the deposit accession number 08020602, 08020603 or 08020604 corresponding to filing references QOR/RE07-169, QOR1 CJ07 and CORECB/SF08-06, respectively. Further inventive cell lines have the characteristic features, like ability to propagate, cell cycle pattern, telomerase activity, caryotype, chromosome pattern or telomere length as said deposited cell lines and of course being a continuous cell line.

The present invention is further illustrated by the following examples without being limited thereto.

EXAMPLES

Example 1

Temporally Different Radiation of Vero Cells with UV Light for Producing Mutants Materials:
  TC-Vero medium
  N1-buffer
  Trypsin (1:10 dilution)
  Trypsin inhibitor
  6-well plates, Corning Cat. No. 3516
  25 cm$^2$ T-Flask, Nunc Cat. No.: 163371
  UV lamp, VL 50C, 240 nm Grid-Tube, 50 W, company Vilber-Lourmet Procedure:

Set-up is done in 6-well plates with 1×10$^6$ cells/well and 5 ml of medium volume (in double set-up). A total of 7 plates (each time 2 wells/plate) is set up.

After 24 h there was a good monolayer culture.

The 5 ml of medium were drained off to 1 ml, and the opened plates were irradiated with UV light (distance of the plates from the UV lamp=9 cm)

| plate A: | 15 min |
| plate B: | 30 min |
| plate C: | 45 min |
| plate D: | 60 min |
| plate E: | 90 min |
| plate F: | 120 min |
| plate G: | control, no irradiation |

After irradiation, the cells of both wells are trypsinized (1 ml Trypsin+0.5 ml trypsin inhibitor/well), wherein the cells of the 1$^{st}$ well are used for determination of cell count (CC) and viability, and the cells of the 2$^{nd}$ well are passaged in 25 cm$^2$ roux with 10 ml of medium.

| Test no. | Irradiation time | TCC/well [×10$^6$] | Bürker-Türk viab. [%] |
| --- | --- | --- | --- |
| A | 15 min | 1.50 | 60.8 |
| B | 30 min | 1.25 | 27.9 |
| C | 45 min. | 1.15 | 5.6 |
| D | 60 min | 0.95 | 23.6 |
| E | 90 min | 0.55 | not determined |
| F | 120 min | 0.30 | not determined |
| G | control | 1.25 | 94.2 |

T-flask 25 content was trypsinized, the TCC and viability is determined using Cedex:

| Test no. | TCC/Roux [×10$^6$] | Viab. [%] | Microscopic picture |
| --- | --- | --- | --- |
| A | 0.80 | 23.2 | spheroidal cells, no adherence |
| B | 0.60 | 18.8 | cells in the supernatant, no adherence |
| C | 0.60 | 34.4 | individual cells in the supernatant, no adherence |
| D | 0.50 | 25.0* | only cell debris left |
| E | 0.50 | 22.7* | only cell debris left |
| F | 0.40 | 11.1* | only cell debris left |
| G | 1.80 | 96.6 | good monolayer, 95-100% |

*the actual values are lower since the cell count in the Cedex is too low for correct cell-count determination!!!

Example 2

UV Irradiation of Avian Cells

The aim of this study was to investigate the potential use of UV-light treatment as a tool for the generation of continuous cell lines suitable for vaccine production.

Primary chicken and quail embryos were used as starting material for production of initial primary monolayer cultures. Quality controlled cell cultures derived therefrom were used for derivation procedure based on the UV light exposure.

Exposure of primary cells to UV light (254 nm). The continuous cell line was developed from primary cells of bobwhite quail or chicken embryos by means of UV irradiation.

Figure 1:
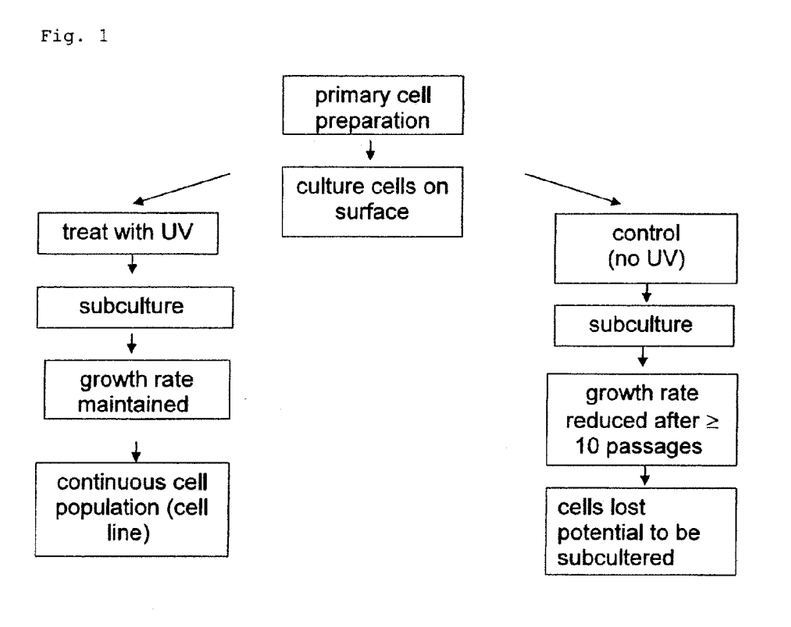
FIG. 1 shows the scheme of the UV treatment procedure.
Figure 2:
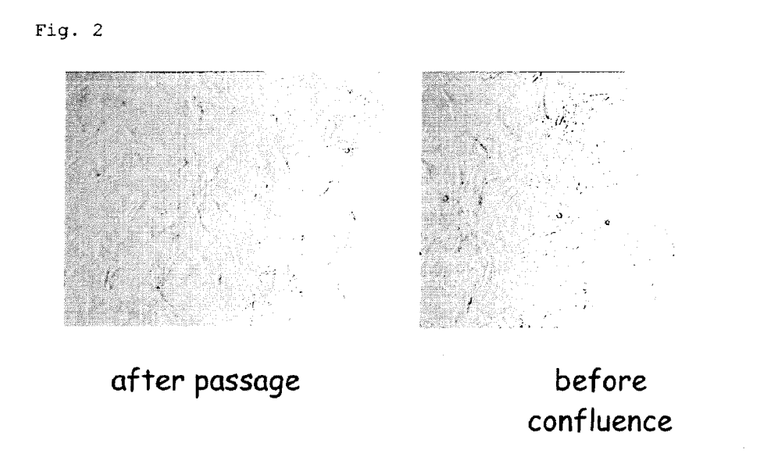
FIG. 2 shows continuous quail cell cultures
Figure 3:
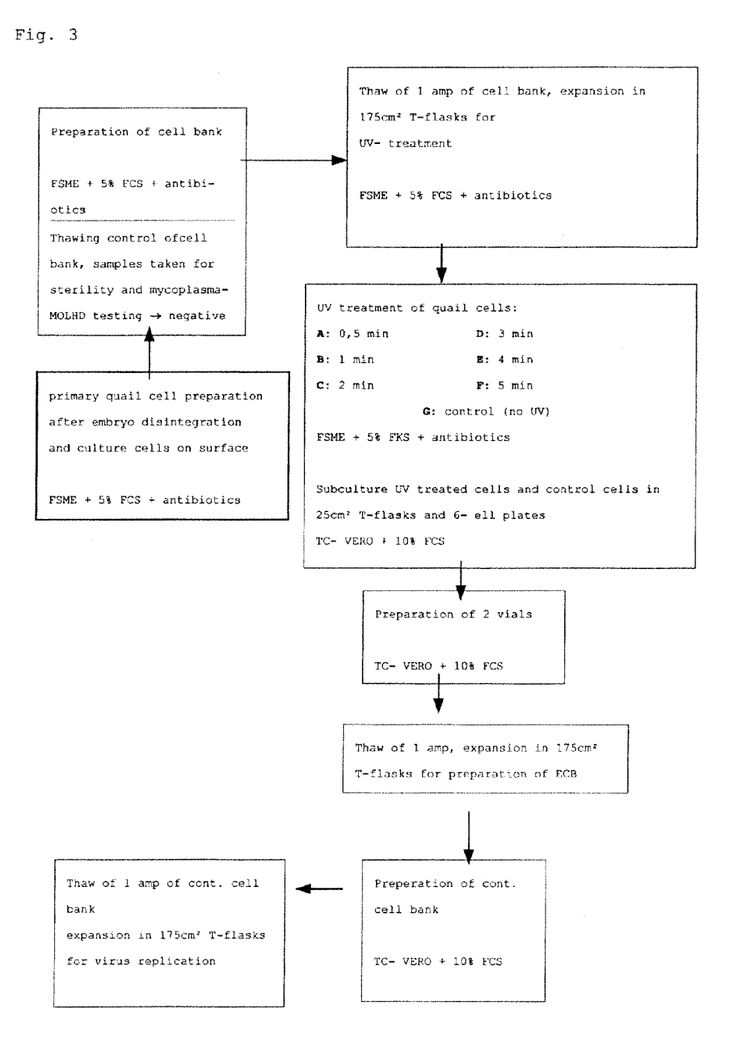
FIG. 3 shows the phylogenetic tree, and treatment route of producing a continuous quail cell line.

The detailed course of development of the cell line derived from the primary cells of quail embryos up to the production of safety banks is illustrated in FIG. 3 in the form of a phylogenetic tree.

As starting material for UV irradiation, in each case one ampoule of the first evaluation cell banks (chicken, Japanese quail and bobwhite quail) which originate from a cell preparation of the chicken embryos, embryos of the Japanese quail and of the bobwhite quail (mixed culture of disintegrated complete embryos) was thawed.

The set-up for UV irradiation was done in 6-well plates with a cell seed of 1×10$^6$ cells/well and 5 ml of medium volume. TBE medium (FSME) with 5% of FBS and antibiotics (penicillin, streptomycin and gentamycin) were used as medium. A total of 7 plates with 2 well/plate each was set up. After 24 h, a uniform monolayer culture could be observed in the wells. For irradiation of the cells, the 5 ml of medium were drained off to 1 ml and the opened plates were irradiated with UV light in the laminar flow bench as follows. The distance of the plates from the UV lamp was 9 cm. A UV lamp of the company Vilber-Lourmet (VL 50C, 240 nm Grid-Tube, 50 W) was used as UV light source.

| plate A: | 0.5 min |
| plate B: | 1 min |
| plate C: | 2 min |
| plate D: | 3 min |
| plate E: | 4 min |
| plate F: | 5 min |
| plate G: | control, no irradiation |

After irradiation, the cells were trypsinized in the wells (1 ml trypsin 1:10 diluted with N1 buffer), wherein 1 ml of the cell suspension (a total of 6 ml) was used for determination of CC and viability, and the remaining cells were passaged with 5 ml of medium in 25 cm$^2$ roux. The results are summed up in the table of this example.

During the first culturing period (about 25-35 days) there were only media exchanges, and morphology and adherence of the cells were optically assessed in the individual tests. Only after island formation of the adherently growing cells in the T-25 flasks had been observed, the cells of tests A-E were trypsinized and transferred to 6-well plates (smaller surface than T-25 flasks) in order to promote a homogeneous, adherent cell colonization. From this point in time, about K40-K50, the cells that had reached a confluence of 80-100% were further passaged in T-25 and T-75 flasks every 6-9 days and set up in 1-2 safety ampoules which served as starting material for producing the evaluation cell banks (about 10 ampoules). Trypsinization and passaging of said cell populations is described in Example 3.

Preparations Used

Medium:

TBE medium (FSME)+5% FBS+mixture of antibiotics (penicillin/streptomycin 100 mg/l and 50 mg/l gentamycin)

TBE medium (FSME)+10% FES

TC Vero medium+10% FBS

N1 buffer

Gamma trypsin

DMSO company Sigma

Abbreviations: CC . . . cell count, T-25/75/175 . . . 25/75/175 cm$^2$ T-flasks,

TABLE

Cell counts and viabilities of the individual tests after irradiation

| Test no. | Irradiation time | CC/ml [×10$^6$] | Bürker-Türk viab. [%] | TCC/well [×10$^6$] |
|---|---|---|---|---|
| A | 30 sec | 0.75 | 87.3 | 0.15 |
| B | 1 min | 0.75 | 79.5 | 0.15 |
| C | 2 min | 0.80 | 84.1 | 0.16 |
| D | 3 min | 0.70 | 90.4 | 0.14 |
| E | 4 min | 0.80 | 80.0 | 0.16 |
| F | 5 min | 0.70 | * | 0.14 |
| G | control | 0.75 | 84.1 | 0.15 |

* not determined

Due to the similar cell-count values and viabilities of the individual test set-ups A-G, no significant difference could be shown with respect to UV-irradiation time of the cells. This is the reason why morphology and adherence of the cultures compared were assessed nearly daily to recognize particularities.

From all test set-ups A-F, the cell population from set-up E showed the best properties of a continuous, adherently growing cell line, such as homogeneous cell structure, culturing in different T-flasks, constant cell growth after several passages, capability for cryoconservation and suitability for virus propagation (e.g. MVA virus).

In the case of quail cells, the cell population from set-up F could not be successfully cultured. Reduced cell growth with inhomogeneous cell-lawn formation (large wholes) could be observed after more than 6 passages with the cells (test G) which had not been irradiated with UV light. From passage 16 on, the cells lost their division capability and could not be cultured any longer. All in all, similar results could be reached with quail and chicken cell tests.

Example 3

Trypsinization and Passaging of Cells

Trysinization and passaging of the adherently growing quail cells were done in a passaging scheme similar to that usually used for Vero cells. After pouring off the culture medium, a washing step is performed with N1 buffer, thereafter, the culture is covered with layer(s) of the corresponding amount of gamma trysin, diluted 1:10, and is incubated at a temperature (with 6-well plates and T-25 (T-25 ... 25 cm$^2$ T-flasks) room temperature is sufficient) of 37° C. until the cells detach from the culturing vessel (by soft knocking). Addition of the trypsin inhibitor to stop the effect of trypsin is not necessary due to the FBS contained in the culture medium. Subsequently, the cells are transferred to a new culture medium and are divided up into further culturing vessels in correspondence with the respective splits, and are, again, left to grow.

The following table indicates the amounts used during trypsinization.

| culturing vessel | N1 buffer | Gamma trypsin (1:10 diluted with N1 buffer) |
|---|---|---|
| 6-well plate | 2 ml | 1 ml |
| 25 cm$^2$ T-flask | 5 ml | 1 ml |
| 75 cm$^2$ T-flask | 10 ml | 1 ml |
| 175 cm$^2$ T-flask | 20 ml | 2 ml |

Example 4

UV-C Dosimetry for Cell Immortalization with the UV lamp VL 50C

Figure 4:
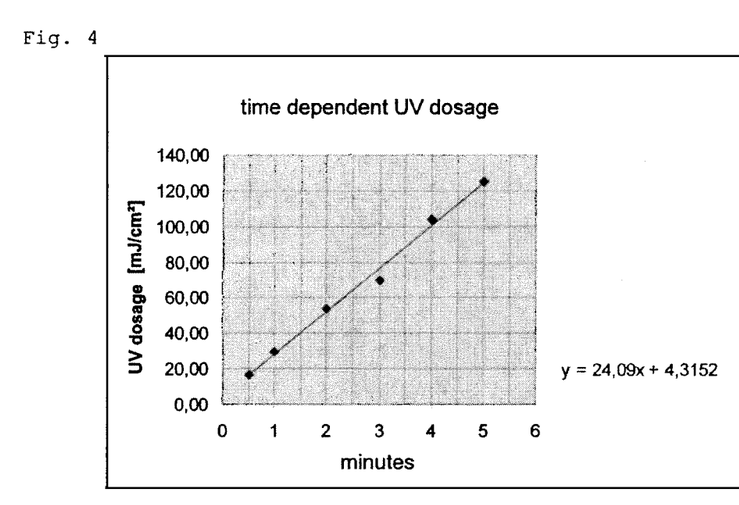
FIG. 4 shows a correlation of the UV dosage to the irradiation time with the set-up used to produce continuous cells.

The dosage to obtain continuous cell lines with UV irradiation was measured. The dosimetry set up was similar to the set up for cell treatment. The radiation with UV-C light causes a transformation of potassium iodide and potassium iodate dissolved in buffer solution into brown-yellow tri-iodide. Tri-iodide has its absorption maximum at 352 nm and can be measured quantitatively in a spectral photometer. This principle allows to measure the UV dosage applied during cell monolayer exposure depending on exposure time. Therefore, based on measurements in 6-well plates, an exposure time of from 0.5 to 5 minutes corresponds to an UV dosage of from 20 to 120 mJ/cm$^2$ (FIG. 4).

Dosimetry is done as precisely as possible, as is the cell-line test. In each case 1 ml of the model solutions with absorption coefficients (367 mn) of about 2.5/cm, 4.5/cm and 7.5/cm is irradiated in one well of the 6-well plate. Each model solution is irradiated 6 times. Irradiation times=30 sec, 1 min, 2 min, 3 min, 4 min und 5 min. In order to find out the exact dosage for the respective irradiation time, the OD (253.7 nm) of the medium used is determined.

Materials Used:
portable UV lamp, VL50C, 254 nm, 50 W, company Vilber-Lourmat
Spectral photometer, company Therma, Device No.: PA5007-012MM
6-well plate
Boric acid 99.9%, company Riedel-de Haen, Lot No.: 60460
NaOH pellets, company Baxter, Lot No.: 318608
PVP K17 PF (polyvinyl-pyrrolidon Collidon K17), company Basf, Lot No.: 30408609T0
Potassium iodide, company Sigma Aldrich, Lot No.: P2963-500G
Potassium iodate, company Merck, Lot No.: K32577451622
TC VERO medium (VT), Charge: ORSFVTC0700401
WFI water, company Baxter, PP2
Three model solutions are prepared in sufficient amounts.

TABLE 1

Composition of the model solutions

| Reagent | Model solution 1 | Model solution 2 | Model solution 3 |
|---|---|---|---|
| Boric acid | 6.18 g/l in Aqua dest. dissolve | | |
| NaOH pellets | desired value pH: 9.15; about 2 g/l | | |
| PVP K17 PF | 2.414 g/l | | |
| Potassium iodide purest | 1.41 g/l | 2.57 g/l | 4.30 g/l |
| Potassium iodate purest | 0.3 g/l | 0.55 g/l | 0.92 g/l |

The model solutions can be stored in a dark place until they are used but at least up to 47 days.

60 ml each are taken from model solutions 1, 2 and 3 to produce a calibration curve. Protected from incident light, these samples are sent to IBC which establishes the calibration curve 100 ml each are transferred from model solutions 1, 2 und 3 into Schott flasks and are protected from incident light. The portable UV lamp VL 50C ist placed on a framework. The distance between the table plate and the bottom side of the portable UV lamp is 9 cm. The portable UV lamp is adjusted such that the filter points to the table plate (i.e. downwards).

The portable UV lamp is turned on 30 minutes before it is used.

The 3 Schott flasks with the 100 ml of model solutions 1, 2 and 3, pipettes, pipettboy, an empty Schott flask and three 6-well plates are prepared. 1 ml of model solution 1 is pipetted into the left upper well of a 6-well plate. This well is placed below the portable UV lamp without a cover such that it is positioned centrally below the filter. After 30 sec of irradiation, the well is quickly removed from its position below the portable UV lamp. 370 µl of the irradiated 1-ml solution are transferred to a thin-layered silica cuvette and the OD367 nm is determined within 5 minutes. The same is measured three times and recorded. The mean value of these 3 values is determined. If a value measured is beyond the calibration region of the photometer, correspondingly, a cuvette with a different layer thickness will be used. The supernatant in the well is sucked off and discarded.

These steps are repeated for all irradiation times. Based on the obtained curve functions and OD (253.7 nm) of the VT medium, the respective UV dosage [mJ/cm$^2$] is calculated far from 30 seconds to 5 minutes. The results are presentend in the following table.

TABLE

| UV dosage calculated based on the respective curve functions: | |
|---|---|
| irradiation time | 30 seconds |
| potential curve function | $y = 21.767x^{-0.1945}$ |
| A 253.7 VT medium (=x) | 4.01 |
| UV dosage [mJ/cm$^2$] | 16.61 |
| irradiation time | 1 minute |
| potential curve function | $y = 56.953x^{-0.4709}$ |
| A 253.7 VT medium (=x) | 4.01 |
| UV dosage [mJ/cm$^2$] | 29.61 |
| irradiation time | 2 minutes |
| potential curve function | $y = 98.154x^{-0.4322}$ |

TABLE-continued

| UV dosage calculated based on the respective curve functions: | |
|---|---|
| A 253.7 VT medium (=x) | 4.01 |
| UV dosage [mJ/cm$^2$] | 53.86 |
| irradiation time | 3 minutes |
| potential curve function | $y = 147.31x^{-0.5363}$ |
| A 253.7 VT medium (=x) | 4.01 |
| UV dosage [mJ/cm$^2$] | 69.95 |
| irradiation time | 4 minutes |
| potential curve function | $y = 2127x^{-0.5159}$ |
| A 253.7 VT medium (=x) | 4.01 |
| UV dosage [mJ/cm$^2$] | 103.90 |
| irradiation time | 5 minutes |
| potential curve function | $y = 264.53x^{-0.5377}$ |
| A 253.7 VT medium (=x) | 4.01 |
| UV dosage [mJ/cm$^2$] | 125.36 |

As can be seen from this table, the curve function of the dosage is $y=24.09x+4.3125$. X is the irradiation time in minutes and y is the dosage in mJ/cm$^2$ (FIG. 4).

Example 5

Virus Production in Continuous Cells

MVA, r-MVA, TBE and Influenza were propagated in continuous quail cells. Roller bottle cultures of quail cells were established as described above. Cultures were infected with (GMP) MVA, TroVax, TBE and Influenza virus. A MOI was chosen according to the current MVA production process. Viral products were harvested after 3 to 4 days. AS culture medium TC-Vero 10% FBS was used during incubation at incubation 32° C.

Infect.: carried out with 10 ml after 1 h at final volume (60 ml)
  TBE: 50 µl virus
  MVA: 250 µl virus
  New Caledonia (NC): 50 µl
Abbreviation: KXX . . . day of culture XX
Taking of samples: 3×1 ml sample, NOVA, NaBr— with NC, HA, micro-photography
TBE

| day | glucose [g/l] | glutamine [g/l] | lactate [g/l] | NH4 [mg/l] | pH | CO2 [%] | virus titer lg pfu/ml | TBE-Elisa µg/ml | CPE % | TBE-HA HAU/200 µl |
|---|---|---|---|---|---|---|---|---|---|---|
| 1 | x | x | x | x | x | x | x | x | 0 | x |
| 2 | 2.83 | 0.31 | 0.33 | 21 | 7.36 | 5.8 | neg | 0.02 | 0 | 16 |
| 3 | 2.71 | 0.27 | 0.4 | 26 | 7.32 | 6 | 6.34 | 0.08 | 0 | 16 |
| 4 | 2.47 | 0.2 | 0.59 | 47 | 7.36 | 5.1 | 6.87 | 0.21 | 0 | 64 |

MVA

| day | glucose [g/l] | glutamine [g/l] | lactate [g/l] | NH4 [mg/l] | pH | CO2 [%] | TCID$_{50}$ titer | | CPE % |
|---|---|---|---|---|---|---|---|---|---|
| 1 | x | x | x | x | x | x | x | x | 0 |
| 2 | 2.64 | 0.31 | 0.44 | 20 | 7.31 | 6.1 | x | x | 0 |
| 3 | 2.6 | 0.27 | 0.58 | 23 | 7.26 | 6.1 | x | x | 0 |
| 4 | 2.36 | 0.21 | 0.74 | 43 | 7.35 | 4.9 | 7.02e8 V/ml | x | 0 |

New Caledonia

| day | glucose [g/l] | glutamine [g/l] | lactate [g/l] | NH4 [mg/l] | pH | CO2 [%] | NaBr mm | HA | CPE % |
|---|---|---|---|---|---|---|---|---|---|
| 1 | x | x | x | x | x | x | x | x | 20 |
| 2 | 2.76 | 0.3 | 0.34 | 21 | 7.32 | 6.2 | x | 3 = 8HAU | 70 |

-continued

| day | glucose [g/l] | glutamine [g/l] | lactate [g/l] | NH4 [mg/l] | pH | CO2 [%] | NaBr mm | HA | CPE % |
|---|---|---|---|---|---|---|---|---|---|
| 3 | 2.82 | 0.26 | 0.38 | 25 | 7.34 | 5.7 | 0 | 5 = 32HAU | 100 |
| 4 | 2.63 | 0.19 | 0.48 | 45 | 7.41 | 5 | 0.00E+00 | 5 = 32HAU | 100 |

Control

| day | glucose [g/l] | glutamine [g/l] | lactate [g/l] | NH4 [mg/l] | pH | CO2 [%] | NaBr mm | HA | CPE % |
|---|---|---|---|---|---|---|---|---|---|
| 1 | x | x | x | x | x | x | x | x | 0 |
| 2 | 1.78 | 0.16 | 1.24 | 31 | 7.03 | 6.3 | x | x | 0 |
| 3 | 1.24 | 0.12 | 1.42 | 34 | 6.87 | 6.9 | x | x | 0 |
| 4 | 1.52 | 0.11 | 1.61 | 53 | 6.94 | 4.9 | x | x | 0 |

Virus titer achieved for MVA and r-MVA grown in roller bottle experiments:

| Virus | $TCID_{50}$/ml |
|---|---|
| MVA | $8 \times 10^8$ |
| r-MVA (TroVax) | $9 \times 10^8$ |

Virus titer achieved for TBE and Influenza grown in roller bottle experiments:

| Virus | Titer (log pfu/ml) | HA (HAU/50 µl) | CPE (%) |
|---|---|---|---|
| TBE | 6.9 | 64 | 100 |
| New Caledonia | not determinated | 32 | 100 |

Example 6

F-Pert Assay of Different Cell Cultures

The F-Pert assay allows to detect reverse transcriptase activity by PCR and is necessary for safety validation. Different cultures (Vero (neg. control), primary chicken (pos. control), continuous quail and continuous chicken cells) were prepared according to the same procedure. Culture supernatants were harvested and processed for F-Pert quality control testing
Results F-Pert Testing

| Cell Culture | F-Pert |
|---|---|
| Vero (control) | negative |
| CEC (primary chicken cells) | positive |
| quail cells (4 different cultures) | negative |
| chicken cells (2 different cultures) | negative |

The invention claimed is:

1. A method for production of a continuous avian cell line comprising irradiating cultured isolated primary avian cells with a UV light having a wavelength between 200 nm to 300 nm and with a dose from about 20 mJ/cm$^2$ to about 105 mJ/cm$^2$, wherein the irradiation time is from 30 seconds to 4 minutes, and selecting cells capable to proliferate after at least 20 passages as cells of a continuous avian cell line.

2. The method of claim 1 wherein said UV light dosage is at least 50 mJ/cm$^2$.

3. The method of claim 1 wherein selecting said cells comprises at least 40 passages.

4. The method of claim 1 wherein said cells are attached to a surface or are in suspension.

5. The method of claim 1 wherein said cells are cells of an embryo.

6. The method of claim 1 wherein said cells are a mixed culture of more than one type of tissue.

7. The method of claim 1 wherein said cells are in a monolayer.

8. The method of claim 1 further comprising infecting said cells with a virus under conditions which permit virus proliferation.

9. The method of claim 8 wherein said virus is selected from baculovirus, poxvirus, adenovirus, papovavirus, parvovirus, hepadnavirus, coronavirus, flavivirus, togavirus, astrovirus, picornavirus, retrovirus, orthomyxovirus, filovirus, paramyxovi-rus, rhabdovirus, arenavirus, and bunyavirus.

10. The method of claim 8 wherein said virus is selected from modified vaccinia virus Ankara (MVA), tick-borne encephalitis (TBE) virus, Yellow fever virus, West Nile virus, New Caledonia virus or an influenza virus.

11. The method of claim 1 further comprising transfecting said cells with a nucleic acid encoding a gene product, growing said cells under conditions which permit production of said gene product.

12. The method of claim 1 wherein said cells of said cell line are adapted for growth in serum free media.

13. The method of claim 12 wherein said medium is selected from DMEM/HAM's F12, RPMI, MEM, BME, Waymouth's medium, an oligopeptide free medium, a chemically defined medium or a combination thereof.

14. The method of claim 1 wherein said cells of said cell lines are selected for being non-tumorigenic and/or non-carcinogenic.

15. The method of claim 1, wherein the dose is from about 70 mJ/cm$^2$ to about 105 mJ/cm$^2$.

16. The method of claim 8, further comprising collecting said virus.

17. The method of claim 11, further comprising collecting said gene product.

* * * * *